United States Patent [19]

Phatak et al.

[11] Patent Number: 4,731,104

[45] Date of Patent: Mar. 15, 1988

[54] METHOD FOR CONTROLLING YELLOW NUTSEDGE USING *PUCCINIA CANALICULATA*

[75] Inventors: Sharad C. Phatak; Donald R. Sumner; Homer D. Wells; Durham K. Bell; Norman C. Glaze, all of Tifton, Ga.

[73] Assignee: The United States of America as represented by the Secretary of Agriculture, Washington, D.C.

[21] Appl. No.: 778,048

[22] Filed: Sep. 20, 1985

Related U.S. Application Data

[63] Continuation-in-part of Ser. No. 591,367, Mar. 20, 1984, abandoned.

[51] Int. Cl.[4] ............................................. A01N 63/04
[52] U.S. Cl. .......................................................... 71/79
[58] Field of Search ............................................ 71/79

[56] References Cited

PUBLICATIONS

Templeton, Biological Control of Weeds with Plant Pathogens, John Wiley and Sons (1982), Chapter 3, pp. 29, 31, 35 and 40.

*Primary Examiner*—Catherine L. Mills
*Attorney, Agent, or Firm*—M. Howard Silverstein; John D. Fado

[57] ABSTRACT

A biological method for either controlling or eliminating yellow nutsedge in agricultural fields is disclosed. An agricultural field which contains yellow nutsedge is inoculated with a sufficient amount of an effective strain of rust fungus *Puccinia canaliculata* and a carrier to an epidemic. As a result of reducing competition from the yellow nutsedge and inhibiting reproduction, the yellow nutsedge is either controlled or eliminated. Best results occur when the agricultural field is inoculated in the spring of the year. Application methods include: spraying, granular, irrigation, wind-carried, or air-dropped.

2 Claims, No Drawings

METHOD FOR CONTROLLING YELLOW NUTSEDGE USING PUCCINIA CANALICULATA

CROSS-REFERENCE TO RELATED APPLICATIONS

This is a continuation-in-part of application Ser. No. 591,367, filed Mar. 20, 1984, abandoned.

BACKGROUND OF THE INVENTION (1) Field of the Invention

This invention relates to a method for controlling yellow nutsedge using the rust fungus.

(2) Description of the Prior Art

Yellow nutsedge, *Cyperus esculentus L.*, is thought to be one of the world's most troublesome weeds. This weed has been a serious pest for many decades. In recent years it has spread rapidly throughout the United States and is now the most troublesome perennial weed in most of the Midwest.

Yellow nutsedge reproduces prolifically. One tuber plated in a field in Minnesota produced 1900 plants and 6900 tubers in 1 year. In Georgia 622 tubers were produced from one tuber in 17 weeks.

In spite of considerable effort, biocontrol methods for yellow nutsedge have not shown much success. Rust caused by *Puccinia Canaliculata* was first described in 1832. In 1906, it was demonstrated that Xanthium sp. was an alternate host, and indication that the pathogen is a macrocyclic heteroecious rust. Another possible alternate host is giant ragweed, *Ambrosia trifida L.* To our knowledge, no research has been reported on using this rust fungus to control yellow nutsedge. Researchers have observed the rust on yellow nutsedge in many locations in the United States and Canada. However, it usually does not appear until August and does not increase substantially until September. By then, the nutsedge has produced new seed and tubers and its life cycle is unaffected by the rust.

SUMMARY OF THE INVENTION

This invention provides a process for controlling or eliminating yellow nutsedge in the agricultural field, and comprises inoculating the agricultural field that is contaminated with yellow nutsedge with a sufficient amount of an effective strain of the rust fungus *Puccinia canaliculata*, and a carrier to initiate an epidemic and thereby control or eliminate the yellownutsedge as a result of reducing competition from the yellow nutsedge and also by inhibiting reproduction.

DESCRIPTION OF THE PREFERRED EMBODIMENTS

*Puccinia canaliculata* is on deposit as *Puccinia canaliculata* ATCC (#40199) at the following location: American Type Culture Collection, 12301 Parklawn Drive, Rockville, MD 20852. Documentation of the organism *Puccinia canaliculata* can be found in J. C. Arthur, *Manual of the Rusts in the United States and Canada* (Purdue Research Foundation, Lafayette, Ind., 1934, page 180).

Earliest experimentation of effectiveness of controlling yellow nutsedge with the rust fungus *Puccinia canaliculata* was conducted after an epiphytotic of rust was observed on a dense strand of yellow nutsedge in September 1978 on applicant's research farm near Tifton, Ga. Later in August-September, 1979 a severe rust epiphytotic developed on this nutsedge. In 1980, weekly observations were carried out and found a few plants in June with rust. The infected nutsedge was located in vegetable research plots that had been sprayed weekly with fungicides. The infected plants were then potted and placed among a thick stand of yellow nutsedge (0.5ha) without any symptoms 7 Km away. The new area was not sprayed with fungicides. Rust pustules were evident on plants at the new site within 12 days. An epiphytotic developed within 4 weeks over the entire area. This early experiment indicated that yellow nutsedge could be controlled to some extent using the fungus.

EXAMPLE 1

The following experiment was carried out to conclusively show the effectiveness of using the rust fungus *Puccinia canaliculata* ATCC #40199 to control yellow nutsedge:

Rust was maintained on infected plants in a greenhouse during the winter months. Pots of nutsedge plants with only one to two visible rust pustules were placed in four plots (13×13 m) on May 1, 1981 as soon as nutsedge appeared in the plots. Within 10 days pustules were observed on all nutsedge plants within 1 m of the original plants and within 7 m in 14 days. There was no visible infection for up to 17 days on the windward side. The major direction of spread was eastward, an indication of leeward spore movement. Twenty-eight days later rust was observed 130 m away on the leeward side of the original inoculum. By the first week of June, an epiphytotic developed with over 90 percent of the nutsedge leaves dead or dying. During this period, rust released in yellow nutsedge under a corn canopy moved only 3 m. This result demonstrates that wind is essential for the spread of rust. Later, manual spraying of the rust was conducted to improve speed of spreading and control of inoculation.

Weekly observations indicated that dehydration of nutsedge root occurs soon after a few pustules appear on the plant. General dehydration of the plant follows root dehydration; this is reflected in a higher percentage of dry matter in rust-infected plants. (Table 1).

TABLE 1

Effect of rust fungus on nutsedge 60 days after rust release. Each mean is the average of four replications. In all cases listed, the means in each column were different at the 5 percent level (t-test).

| Nutsedge Sample | Leaf Area Diseased (%) | Root Growth (%) | Fresh Weight Per Plant (g) | Dry Weight Per Plant (g) | Dry Matter (%) |
|---|---|---|---|---|---|
| Rust-Infected | 78.5 | 18.5 | 5.9 | 1.8 | 29.8 |
| Control* | 10.5 | 87.0 | 13.7 | 2.9 | 21.1 |

*Weekly application of chlorothalonil.

Old parent tubers on infected plants were also dehydrated. Rust reduced the dry weight and fresh weight of nutsedge. (See Table 1 Supra). Flowering and tuber formation of nutsedge were inhibited in rust-infected areas for up to 16 weeks after inoculation, whereas chlorothalonil-sprayed nutsedge controls flowered profusely and produced tubers. (See Table 2).

TABLE 2

Effect of rust fungus on nutsedge tuber formation, flowering, and survival 90 and 120 days after rust release. The numbers in parentheses represent the percentages of the totals. Each mean is the average of four replications. Each pair of rust-control means is different at the 5 percent level (t-test).

| | Number per 0.93 m² | | | |
|---|---|---|---|---|
| | 90 Days | | 120 Days | |
| Nutsedge | Rust Infected | Control* | Rust Infected | Control* |
| Tubers | | | | |
| Old | 169 | 132 | 167 | 108 |
| New | 17 (9) | 60 (31) | 16 (9) | 63 (37) |
| Plants | | | | |
| Live | 112 | 201 | 144 | 313 |
| Dead | 91 (45) | 4 (2) | 122 (46) | 6 (2) |
| Inflorescences | 0 | 23 | 0 | 83 |

*Weekly application chlorothalonil.

Rapid dehydration and substantial reduction or elimination of normal vegetative and sexual reproductive processes, even with moderate rust infection, suggests the production of a biologically active substance or substances.

The rust may be applied by wind-carried particles, granularly applied, sprayed, irrigation, air dropped or from pesticide delivery systems.

The rust is adapted to a wide range of climatic conditions. Rust epiphytotic developed over several hectares from a series of releases throughout the growing season under all conditions where nutsedge was growing. The reported range of this rust is from Massachusetts to Nebraska, southward to Florida and west to California; it is also found in Mexico, Central and South America, the West Indies, and Hawaii.

*Puccinia canaliculata* is specific on the genus Cyperus. It has been reported only on a number of weeds belonging to the genus Cyperus including yellow and purple nutsedge. (J. C. Arthur, Manual of the Rusts in the United States and Canada, Purdue Research Foundation, Lafayette, Ind., (1934) p. 438). No rust was observed on corn, soybean, peanut, tomato, pepper, okra, snap bean, lima bean, cucumber squash, watermelon, southern pea, and cotton in the areas where yellow nutsedge surrounding these crops were covered with rust. Thus, this rust organism satisfies all the requirements for biological control agents outlined by: W. C. Shaw, Weed Science 30 (Suppl.) 2 (1982).

In conslusion, the above experimental example given, clearly shows that the rust caused by *Puccinia canaliculata* ATCC #40199 provides a valuable tool for the control of yellow nutsedge.

We claim:

1. A method of biologically controlling yellow nutsedge comprising: inoculating in the spring of the year an agricultural field containing said yellow nutsedge with a sufficient amount of a strain of the rust fungus *Puccinia canaliculata* identified as ATCC #40199 and a carrier to initiate an epidemic and thereby control or eliminate said yellow nutsedge as a result of reducing competition from the yellow nutsedge and inhibiting reproduction.

2. The method of claim 1 wherein the rust fungus *Puccinia canaliculata* ATCC #40199 is applied to the agricultural field by either: spraying, granular applicators, irrigation, air-dropped, or wind-carried.

* * * * *